US006987100B2

(12) United States Patent
Tanaka et al.

(10) Patent No.: US 6,987,100 B2
(45) Date of Patent: *Jan. 17, 2006

(54) PHARMACEUTICAL COMPOSITIONS FOR TREATING BONE LESIONS IN MULTIPLE MYELOMA

(75) Inventors: Shohei Tanaka, Ibaraki (JP); Utane Matsukawa, Ibaraki (JP); Hironobu Asano, Ibaraki (JP)

(73) Assignee: Astellas Pharm Inc., Tokyo (JP)

( * ) Notice: Subject to any disclaimer, the term of this patent is extended or adjusted under 35 U.S.C. 154(b) by 13 days.

This patent is subject to a terminal disclaimer.

(21) Appl. No.: 10/652,242

(22) Filed: Sep. 2, 2003

(65) Prior Publication Data

US 2004/0043966 A1      Mar. 4, 2004

Related U.S. Application Data

(63) Continuation of application No. 09/869,122, filed as application No. PCT/JP99/07236 on Dec. 22, 1999, now Pat. No. 6,727,233.

(30) Foreign Application Priority Data

Dec. 25, 1998   (JP)   .............................. P.10-368399

(51) Int. Cl.
    *A61K 31/675*   (2006.01)
(52) U.S. Cl. ..................................................... 514/80
(58) Field of Classification Search .................. 514/80
    See application file for complete search history.

(56) References Cited

U.S. PATENT DOCUMENTS 4,990,503 A    2/1991   Isomura et al.

FOREIGN PATENT DOCUMENTS

| EP | 0 647 649 | 4/1995 |
| WO | WO 95/28936 | 11/1995 |
| WO | WO 99/04773 | 2/1999 |

OTHER PUBLICATIONS

Kunzmann et al, *Blood*, 92(10, Suppl. 1, Part 1-2):279B (1998).
Berenson, *Cancer*, 80(8, Supplement):1661-1667 (1997).
Shipman et al, *British Journal of Haematology*, 98:6565-672 (1997).
Roux et al, *Bone*, 15(1):41-49 (1994).
Shipman et al, *Leukemia and Lymphoma*, 32)1-2):129-138 (1998).
Dhodapkar et al, *British Journal of Haematology*, 103:530-532 (1998).

*Primary Examiner*—San-Ming Hui
(74) *Attorney, Agent, or Firm*—Sughrue Mion, PLLC

(57) ABSTRACT

Pharmaceutical compositions for treating bone lesions in multiple myeloma or pharmaceutical compositions for treating multiple myeloma which contain as an active ingredient a compound having both of an effect of suppressing bone resorption accompanying multiple myeloma and an effect of inhibiting multiple myeloma, more particularly, 1-hydroxy-2-(imidazo[1,2-a]pyridin-3-yl)ethane-1,1-bisphosphonic acid or its salt.

4 Claims, 2 Drawing Sheets

PHARMACEUTICAL COMPOSITIONS FOR TREATING BONE LESIONS IN MULTIPLE MYELOMA

This application is a continuation of U.S. application Ser. No. 09/869,122, filed Jun. 25, 2001 now U.S. Pat. No. 6,727,233, which is a 371 of PCT/JP99/07236, filed Dec. 22, 1999, the disclosures of both of which are incorporated herein by reference.

TECHNICAL FIELD

This invention relates to medicines, in particular, pharmaceutical compositions for treating bone lesions in multiple myeloma and pharmaceutical compositions for treating multiple myeloma.

BACKGROUND ART

Multiple myeloma is a neoplastic disease in plasma cells which produce and secrete immunoglobulins (Ig's). The Ig's thus produced are homogeneous proteins called M proteins. The M proteins are observed in the blood in most cases. Known examples of these M proteins include IgG, IgA, BJP, IgD, IgE and IgM. BJP is a protein comprising the L chain of Ig (Bence Jones Protein: BJP) alone. The main focus of this disease resides in bone marrow. Myeloma cells tubercularly proliferate in the bone marrow and thus bone lesions frequently arise. In addition, clinical pictures such as anemia, renal failure and immunodeficiency are observed.

Among all, osteolytic bone lesions are pathognomonic symptoms which are observed in most patients with multiple myeloma. It has been clarified that these bone lesions also affect the prognosis of patients with multiple myeloma and relate to the survival time. Further, bone pain due to bone lesions and pathologic fracture and neuropathy due to spinal compression fracture are causative factors worsening patients' quality of life (QOL). It is known that these bone lesions pathologically include clinical pictures of osteolysis, osteoporosis, bone fracture and combinations thereof. Studies are now under way on the onset mechanism of bone lesions in patients with multiple myeloma. At the present time, it is proposed that parathyroid hormone-related protein (PTHrP), which is a cytokine secreted from myeloma cells and has effects of promoting the formation of osetoclasts and enhancing the activity thereof, might participate therein (Byori to Rinsho, 17(1), 12–17, 1999).

In treating multiple myeloma, use is mainly made of chemotherapies (MP therapy, VAD therapy, C-VAD therapy, polypharmacy, etc.) and chemotherapy with the use of IFN-α. Also, topical radiotherapy and the like are selected depending on the bone lesion conditions (Clinical Oncology, edited by Japan Clinical Oncology Group, published in 1996 by Gan to Kagakuryoho Sha). As the results of the long-term observation on patients with multiple myeloma under chemotherapy, it is reported that a bone resorption marker in urine did not correlate to changes in M proteins due to chemotherapy in many cases, though a tendency toward a decrease in the bone resorption marker was observed in a chemotherapy reaction group showing a decrease of 25% or more in M proteins (Blood, 90, 3743–3750, 1997). Therefore, it becomes more and more necessary to establish a novel therapy for bone lesions accompanying multiple myeloma from the viewpoint of patients' QOL.

As medicines for inhibiting the progress of bone lesions (osteolysis and pathologic fracture) in multiple myeloma, bisphosphonate compounds (hereinafter referred to simply as BP) such as etidronate (7.5 mg/kg body weight, injection), clodronate (800 to 2,400 mg/day, oral, 300 mg/day, injection) and pamidronate (90 mg/4 weeks, intravenous drip) have been marketed in Europe and America. Although it is reported that risedronate (30 mg/day, oral), which is one of BPs, suppressed bone resorption and elevated bone mineral density in patients with multiple myeloma (Bone, Vol. 15, No.1, p. 41–49, 1994), it has not yet approved as a medicine for treating multiple myeloma so far.

In case of using BPs as remedies for bone lesions in multiple myeloma, these compounds are administered in a higher dose than in case of using as remedies for osteoporosis. In addition, BPs are poor in oral absorbability, which considerably elevates the dose of oral BP preparations. The administration of BP in a high dose sometimes worsens the side effects typified by gastrointestinal disorders such as retching, diarrhea and abdominal pain, allergic reaction, hypocalcemia, mental disorders such as insomnia, etc. Therefore, BP preparations are administered to patients parenterally in many cases in practice as parenteral preparations such as injections or intravenous drips. Even clodronate, which is only one BP marketed as oral preparations, should be administered in a very high dose (800 to 2,400 mg/day) and thus burdens a large load to patients. However, BP should be continuously administered to sustain its effects. Therefore, it has been urgently required from the viewpoint of patients' QOL to develop a low-dose oral medicine showing little side effects.

Recently, studies have been made on the anticancer effects of BP's and it is reported that several BP's have an effect of inhibiting cell proliferation in vitro (Britishi J. Haematology, 98, 665–672, 1997), though any clinical usefulness has been proved in none of these cases and some reports rather denying the anticancer effect of BPs are also presented. That is to say, it is reported that pamidronate has been used in a murine model of myeloma, and although no effect on tumor growth was demonstrated, there was evidence of a cytotoxic effect within the bone marrow. It is also reported that risedronate has been used in a murine model of myeloma; however, although there was a clear reduction in bone destruction, no effect on tumor burden was noted (Leukemia and Lymphoma, 32,129–138, 1998). In a patient who was intravenously administered in a higher dose than in prior clinical studies, a transient decrease in a cancer marker was observed. However, it is reported that it is possible that for a cytostatic or even cytotoxic effect to occur, higher dose or more frequent administration of pamidronate is required compared to dosing for its beneficial bone effects (Britishi J. Haematology, 103, 530–532, 1998). Accordingly, it has never been reported hitherto that BPs exert an anticancer effect (i.e., a therapeutic effect on multiple myeloma) in patients with multiple myeloma.

As discussed above, it has been considered that BPs have a therapeutic effect on bone lesions in multiple myeloma but no therapeutic effect on multiple myeloma per se.

On the other hand, it is stated in JP-B-6-99457 and EP 354806 that 1-hydroxy-2-(imidazo[1,2-a]pyridin-3-yl)ethane-1,1-bisphosphonic acid (hereinafter referred to as the compound A) or its salt, which is a bisphosphonic acid compound having a fused heterocycle skeleton, suppresses bone resorption, for example, accelerated bone resorption accompanying Bechet'S disease, hypercalcemia, cancer metastasis into bone, osteoporosis, inflammatory joint diseases such as rheumatoid arthritis, etc. (The term "JP-B" as used herein means an "examined Japanese patent publication".) It is actually confirmed that the compound A exerts a favorable effect of inhibiting bone resorption in osteoporosis. However, no report has been presented so far concerning the therapeutic effect on multiple myeloma and the therapeutic effect on bone lesions in multiple myeloma.

DISCLOSURE OF THE INVENTION

In the course of a study on the pharmacological effects of the compound A, the inventors have unexpectedly found out that it has a therapeutic effect on multiple myeloma per se. That is to say, they have found out that the compound A is a BP of a completely novel type which has an effect of suppressing bone resorption accompanying multiple myeloma and an effect of inhibiting multiple myeloma per se and, therefore, is usable particularly in treating bone lesions in multiple myeloma and multiple myeloma, thereby completing the invention.

Accordingly, the invention relates to pharmaceutical compositions for treating bone lesions in multiple myeloma and pharmaceutical compositions for treating multiple myeloma which contain as the active ingredient a compound having an effect of suppressing bone resorption accompanying multiple myeloma and an effect of inhibiting multiple myeloma.

Now, the invention will be described in detail.

The term "compound having an effect of suppressing bone resorption accompanying multiple myeloma and an effect of inhibiting multiple myeloma" as used in the invention means a compound which has been confirmed as having an effect of suppressing bone resorption accompanying multiple myeloma and an effect of inhibiting the progress of multiple myeloma per se in a clinically acceptable administration dose and administration frequency in human clinics. More particularly speaking, it means the compound A or its salt which has been confirmed as having both of these effects at a low dose in clinical tests as will be described in Examples hereinafter. As the pharmaceutical compositions according to the invention, pharmaceutical compositions of the compound A or its salt for oral administration are preferable and pharmaceutical compositions of the compound A or its salt for oral administration to be used in a dose of 3 to 10 mg per day are still preferable.

The term "treating bone lesions in multiple myeloma" as used in the invention means inhibiting or ameliorating bone lesions accelerated by multiple myeloma, for example, bone pain, osteolysis, bone fracture, skeletal fracture and/or decrease in bone mineral density. Further, amelioration of bone-related symptoms of patients with multiple myeloma accompanying the inhibition or amelioration of these bone lesions also falls within the scope of "treating bone lesions in multiple myeloma". The amelioration of bone-related symptoms of patients with multiple myeloma is exemplified by a decrease in the radiotherapy frequency, a decrease in the dose of analgesics used and a decrease in the frequency of performing surgical operations. Moreover, improvement in the QOL of patients with multiple myeloma accompanying the inhibition or amelioration of these bone lesions also falls within the scope of "treating bone lesions in multiple myeloma". For example, citation may be made of the improvement in the items reported as the result of a questionnaire on the QOL carried out by EORTC (European Organization for Research and Treatment of Cancer) (more particularly, physical activity, role activity, mental activity, social activity, general activity, pain, fatigue, nausea/retching, shortness of breath, insomnia, inappetence, constipation, diarrhea, economic conditions, etc.).

The term "treating multiple myeloma" as used herein means inhibiting or ameliorating the progress of multiple myeloma via the inhibition of the proliferation of myeloma cells. In general, it can be confirmed depending on changes in immunoglobulin (Ig) which is a marker of the progress of myeloma. Moreover, a decrease in the administration frequency of chemotherapeutics and a decrease in the frequency of radiotherapy also fall within the scope of "treating multiple myeloma".

According to the prior reports, although tumor mass is reduced by chemotherapy but bone resorption does not correlate thereto in many cases (ibid., Blood). On the other hand, it is known that a bone resorption marker can be reduced by administering conventionally known BPs to patients with multiple myeloma but tumor mass is not affected thereby (ibid., Leukemia and Lymphoma).

In contrast thereto, it has been clinically confirmed for the first time that the pharmaceutical compositions containing the compound A according to the invention exert a therapeutic effect on multiple myeloma as medicinal BP compositions as well as an effect of inhibiting bone lesions accompanying multiple myeloma, as will be shown by Examples given hereinafter. Because of showing little side effects too, these pharmaceutical compositions are useful as medicinal BP compositions of a novel type satisfying the needs in practical medicine. In particular, it is expected that both of the effect of suppressing bone resorption and the effect of inhibiting myeloma of the compound according to the invention contribute to the treatment of bone lesions in multiple myeloma, thereby achieving more favorable results.

The pharmaceutical compositions according to the invention are applicable to the treatment of multiple myeloma or to the treatment of bone lesions in multiple myeloma. Needless to say, these compositions may be used for both of these purposes.

The pharmaceutical compositions according to the invention can be used together with other anticancer agents such as chemotherapeutics, if needed. While monitoring immunoglobulin (Ig) as a marker indicating the progress of myeloma to thereby confirm the progress of myeloma, the pharmaceutical compositions according to the invention can be administered optionally with the performance of an appropriate chemotherapy or radiotherapy. In case where the pharmaceutical compositions according to the invention are used to inhibit or ameliorate myeloma, it is expected. that the administration frequency of these chemotherapeutics, etc. can be lowered. It is also expected that a more favorable effect of inhibiting myeloma can be established by the combined use of the pharmaceutical compositions according to the invention with other anticancer agents.

The 1-hydroxy-2-(imidazo[1,2-a]pyridin-3-yl)ethane-1, 1-bisphosphonic acid (compound A) or its salt according to the invention is described in JP-B-6–99457 and can be easily obtained by the method described in this document. The term "salt" as used herein is not particularly restricted but involves any pharmacologically acceptable salts. Particular examples thereof include salts with inorganic bases containing metals such as sodium, potassium, magnesium, calcium and aluminum, salts with organic bases such as methylamine, ethylamine, ethanolamine, lysine and ornithine, and ammonium salts. Furthermore, the compound A or its salt may be in any form of various hydrates, solvates or polymorphisms. In case of using as a solid preparation for oral administration, in particular, it is preferable to use 1-hydroxy-2-(imidazo[1,2-a] pyridin-3-yl)ethane-1,1-bisphosphonic acid monohydrate (hereinafter referred to simply as the compound A monohydrate) crystals.

The pharmaceutical compositions according to the invention can be prepared by a conventionally employed method with the use of one or more member selected from among the compound A and its salts, pharmaceutically acceptable carriers, more particularly, drug carriers, excipients and other additives commonly employed in pharmaceutical preparations. The administration may be carried out either by oral administration in the form of tablets, pills, capsules, granules, powders, liquids and the like, or by parenteral administration in the form of injections such as intravenous injections or intramuscular injections, suppositories, percutaneous preparations and the like.

The solid compositions for oral administration according to the invention is used in the form of tablets, powders, granules, etc. In these solid compositions, one or more active ingredients are blended with at least one inert diluent, for example, lactose, mannitol, glucose, hydroxypropylcellulose, microcrystalline cellulose, corn starch, polyvinyl pyrrolidone, aluminum magnesium silicate. These compositions may further contain additives other than the inert diluents in accordance with the conventional methods, for example, lubricants such as magnesium stearate, disintegrating agents such as calcium cellulose glycolate, stabilizers such as lactose or solubilization assisting agents such as glutamic acid or aspartic acid. Tablets or pills may be coated, if necessary, with sugar coating or gastric or enteric films made from sucrose, gelatin, hydroxypropylcellulose, hydroxypropylmethylcellulose, hydroxypropylmethylcellulose phthalate, macrogol, titanium oxide, talc or the like.

The liquid compositions for oral administration involve pharmaceutically acceptable emulsions, solutions, suspensions, syrups, elixirs, etc. These compositions contain inert diluents commonly employed, for example, purified water and ethanol. In addition to the inert diluents, these compositions may further contain auxiliary agents such as humectants and suspending agents, sweeteners, flavors, aromatics and preservatives.

The injection compositions for parenteral administration include sterile aqueous or non-aqueous solutions, suspensions and emulsions. The aqueous solutions and suspensions contain, for example, distilled water for injection and physiological saline. Examples of the non-aqueous solutions and suspensions include propylene glycol, polyethylene glycol, vegetable oils such as olive oil, alcohols such as ethanol, polysorbate 80 and the like. These compositions may further contain auxiliary agents such as preservatives, humectants, emulsifiers, dispersants, stabilizers (for example, lactose), solubilization assisting agents (for example, glutamic acid, aspartic acid). These compositions are sterilized by, for example, filtering through a bacteriostatic filter, adding bactericides or irradiating. It is also possible to produce these compositions by preparing sterile solid compositions and then dissolving in sterile water or sterile solvents for injections before using.

In case of usual oral administration, the daily dose ranges from about 1 to 20 mg, preferably from about 3 to 10 mg and still preferably from about 6 to 9 mg. The daily dose is administered once a day or divided into 2 to 4 doses per day. The dose may be appropriately determined case by case taking the body weight, conditions, age, sex, etc. of the patient into consideration.

In case of intravenous administration, the single dose ranges from about 0.1 to 10 mg, preferably from about 0.1 to 5 mg and still preferably from about 0.5 to 2 mg. The composition can be intravenously dripped in this dose once in 2 to 6 weeks, preferably once in 3 to 5 weeks and still preferably once in 4 weeks over 10 to 60 minutes (preferably 30 minutes). The dose may be appropriately determined case by case taking the body weight, conditions, age, sex, etc. of the patient into consideration.

Next, the effects of the pharmaceutical compositions according to the invention will be illustrated by reference to the following Examples. However, it is to be understood that the invention is not limited thereto.

BEST MODE FOR CARRYING OUT THE INVENTION

EXAMPLE 1

Figure 1:
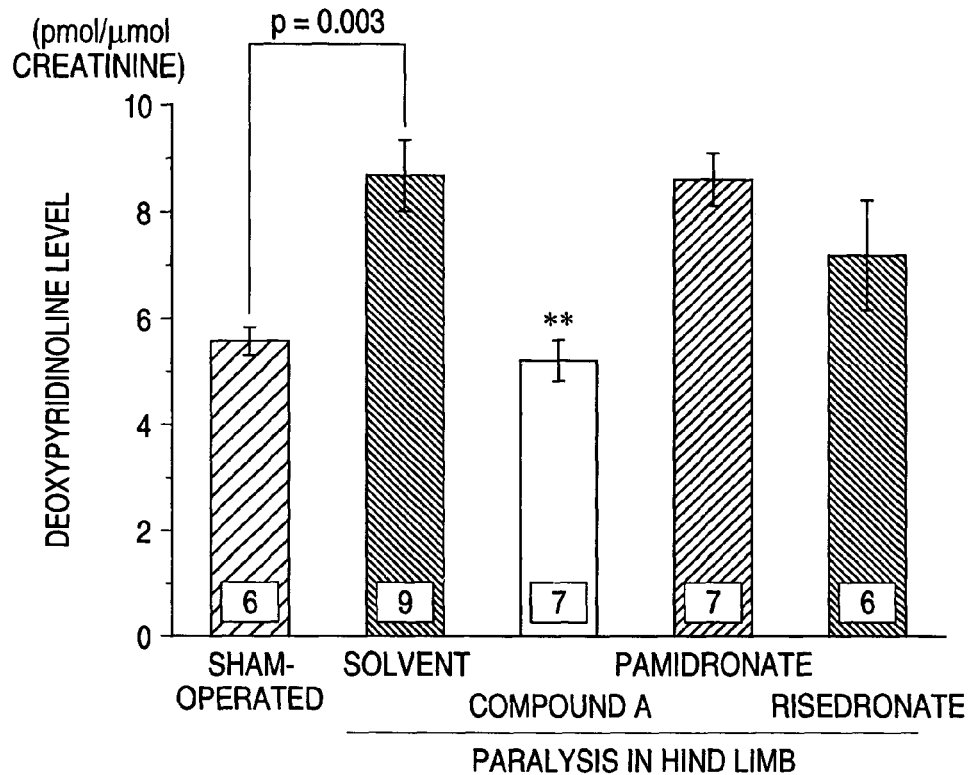
FIG. 1 is a diagram which shows the bone resorption inhibition level with the use of urinary deoxypyridinoline level as a marker. Each column in this figure represents mean±standard error. Number of mice is indicated in columns. Comparisons with the sham-operated group and the solvent group with paralysis in hind limb were performed with the Student's t-test. *significantly different from the solvent group with paralysis in hind limb. (**:Dunnett's multiple range test, $p<0.01$).

Bone Resorption Inhibition Test in Multiple Myaloma Model Animals

<Method>

C.B-17/lcr-scid Jcl mice (male, aged 5 weeks in age) were treated with antiasialo GM1 antibody to lower the NK activity. On the next day, $10^6$ cells/mouse of myeloma cells ARH-77 were transplanted into the left cardiac ventricle of each animal under anesthesia with pentobarbital. About 3 weeks after the transplantation of the tumor, mice suffering from paralysis in hind limbs were selected and aqueous solutions containing compound A monohydrate (0.1 mg/kg), pamidronate (0.1 mg/kg) or risedronate (0.1 mg/kg) and the solvent alone (the solvent group) were intravenously administered to these animals once. On the day 4 after the administration, a physiological saline load (30 ml/kg po) was burdened to these mice and the urine was collected after 6 hours. Since the mice suffering from paralysis in hind limbs could hardly urinate, such an animal was subjected to abdominal section and the urine was directly collected from the bladder. Normal animals (sham-operated group), into the left cardiac ventricle of which PBS (0.1 ml/animal) was injected as a substitute for the myeloma cells, were treated in the same manner. The urinary deoxypyridinoline (Dpyr) level was measured by using a PYRILINKS-D kit (Amersham) and corrected with the urinary creatinine level.

<Results and Discussion>

FIG. 1 shows the results. Compared with the normal mice (sham-operated group), the mice in the solvent group suffering from paralysis in hind limbs due to myeloma showed a large increase in the urinary Dpyr level (a bone resorption marker). In contrast, the increase in the urinary Dpyr level was significantly inhibited in compound A group, i.e., showing a bone resorption level almost comparable to the normal mice (sham-operated group). On the other hand, no significant inhibition was observed in pamidronate or risedronate group. Based on these results, it has been confirmed that the compound A alone can efficaciously inhibit bone resorption accompanying invasion of myeloma in a low dose.

EXAMPLE 2

Lumber Bone Mineral Density Decrease Test in Multiple Myeloma Model Animals

<Method>

(1) Repeated Oral Administration for 6 Days

Similar to Example 1, mice suffering from paralysis in hind limbs were selected 3 weeks after the transplantation of myeloma cells. Then an aqueous solution of the compound A monohydrate (3 mg/kg) (compound A group) and the solvent alone (solvent group) were orally administered once a day for 6 days repeatedly. On the next day of the completion of the administration, a 10% formalin solution was refluxed from the left cardiac ventricle under anesthesia with pentobarbital and the lumber vertebrae was taken out. The bone mineral density in the bone tissue was measured by the DXA method. As Example 1, the normal mice (sham-operated group) were also subjected to the measurement of the bone mineral density.

(2) Repeated Administration for 14 Days

Two weeks after the transplantation of the myeloma cells, the compound A was orally administered for 14 days in doses of 0.03, 0.3 and 3 mg/kg. Then the bone mineral density was measured as in the above (1) but selecting animals suffering from paralysis in hind limbs during the administration period.

<Results>

(1) The Bone Mineral Densities of the Groups Were as Follows.

| | |
|---|---|
| Sham-operated group: | 29.1 ± 0.3 mg/cm² |
| Solvent group: | 22.4 ± 0.7 mg/cm² |
| Compound A group: | 24.7 ± 0.9 mg/cm². |

Figure 2:
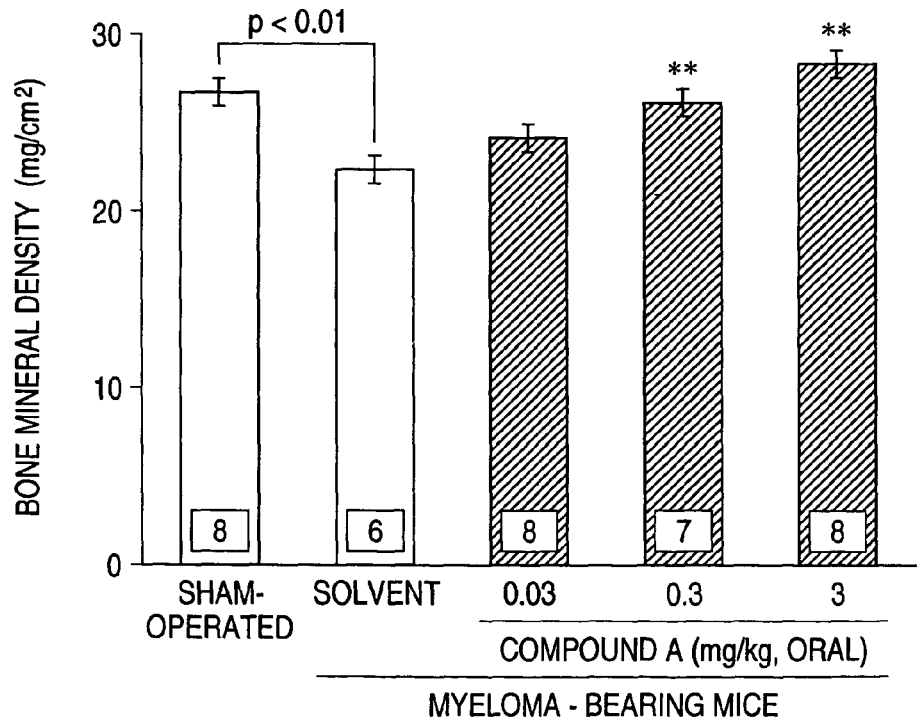
FIG. 2 shows the effects of the oral administration of the compound A on bone mineral density of lumbar vertebrae in Example 2(2).

(2) FIG. 2 Shows the Results.

<Discussion>

Compared with the normal mice (sham-operated group), the mice in the solvent group suffering from paralysis in hind limbs due to myeloma showed an obvious decrease in the lumber bone mineral density. In contrast, the group with the oral administration of the compound A showed a higher bone mineral density than the solvent group. Based on these results, it has been confirmed that the decrease in the bone mineral density accompanying invasion of myeloma was efficaciously suppressed or ameliorated in the compound A group.

EXAMPLE 3

Myeloma Cell Proliferation Inhibitory Test

<Method>

A $5\times10^4$ cells/ml cell dilution of human myeloma cells APH-77, which had been incubated in a culture flask, was prepared by using an RPMI1640 medium (containing 10% of EBS), pipetted in 1 ml portions into a 24-well plate and then incubated in a $CO_2$ incubator at 37° C. After 6 hours, 100 $\mu$l portions of the aqueous solution of the compound A were added to give final concentrations of 0.3 to 1000 $\mu$M (three-fold serial, duplicate samples). After incubating in the $CO_2$ incubator at 37° C. for 4 days, the viable cells were counted with the use of a Cell Counting Kit (Dojin Kagaku). By referring the value of the control prepared by adding PBS as to the cell proliferation inhibitory ratio of 100%, the inhibitory ratios were calculated.

<Results and Discussion>

The compound A inhibited the ARH-77 cell proliferation in a dose-dependent manner. The inhibitory ratio at 100 $\mu$M was 84.2%. These data indicate that the compound A has an effect of inhibiting the proliferation of myeloma cells. It is reported that BPs are accumulated selectively on sites with vigorous bone metabolism, in particular, on the surface of bone under bone resorption, in vivo (Bone, 16(2), 235–245, 1995; J. Clin. Invest. 88, 2095–2105, 1991). It is assumed that the compound A, which is a BP, is also accumulated selectively on bone lesion sites. Accordingly, it is suggested that this proliferation inhibitory effect might participate in the bone lesion-ameliorating effect in the multiple myeloma model as described above.

EXAMPLE 4

Clinical Test 1 (Therapeutic Effects on Multiple Myeloma and Bone Lesions in Multiple Myeloma)

A female patients aged 42 with multiple myeloma was subjected to a chemotherapy (C-VAD therapy) for about 3 months (Jun. 30 to Oct. 3, 1997). After the completion of the chemotherapy, an increase in a bone resorption marker was observed. Since Nov. 12, 1997, film-coated tablets containing 3 mg of the compound A monohydrate were orally administered once a day for 24 weeks continuously.

As a result, the bone resorption marker was favorably decreased and the Dpyr level was lowered after 8 weeks to about 60% of the level before the administration. Also, the blood M protein (IgD) level, i.e., a tumor marker, was considerably lowered with the initiation of the administration of the compound A, as shown in Table 1. Thus, remarkable amelioration of multiple myeloma was indicated.

TABLE 1

Changes in M protein (IgD)

| | Before administration | After 2 weeks | After 4 weeks | After 8 weeks | After 20 weeks |
|---|---|---|---|---|---|
| IgD (mg/dl) | 25.8 | 11.6 | 9.8 | 7.7 | 5.9 |

EXAMPLE 5

Clinical Test 2 (Therapeutic Effect on Bone Lesions in Multiple Myeloma)

To 6 patients (4 males, 2 females) aged 54 to 70 with multiple myeloma, film-coated tablets containing 6 mg of the compound A monohydrate were orally administered once a day for 24 weeks continuously.

Figure 3:
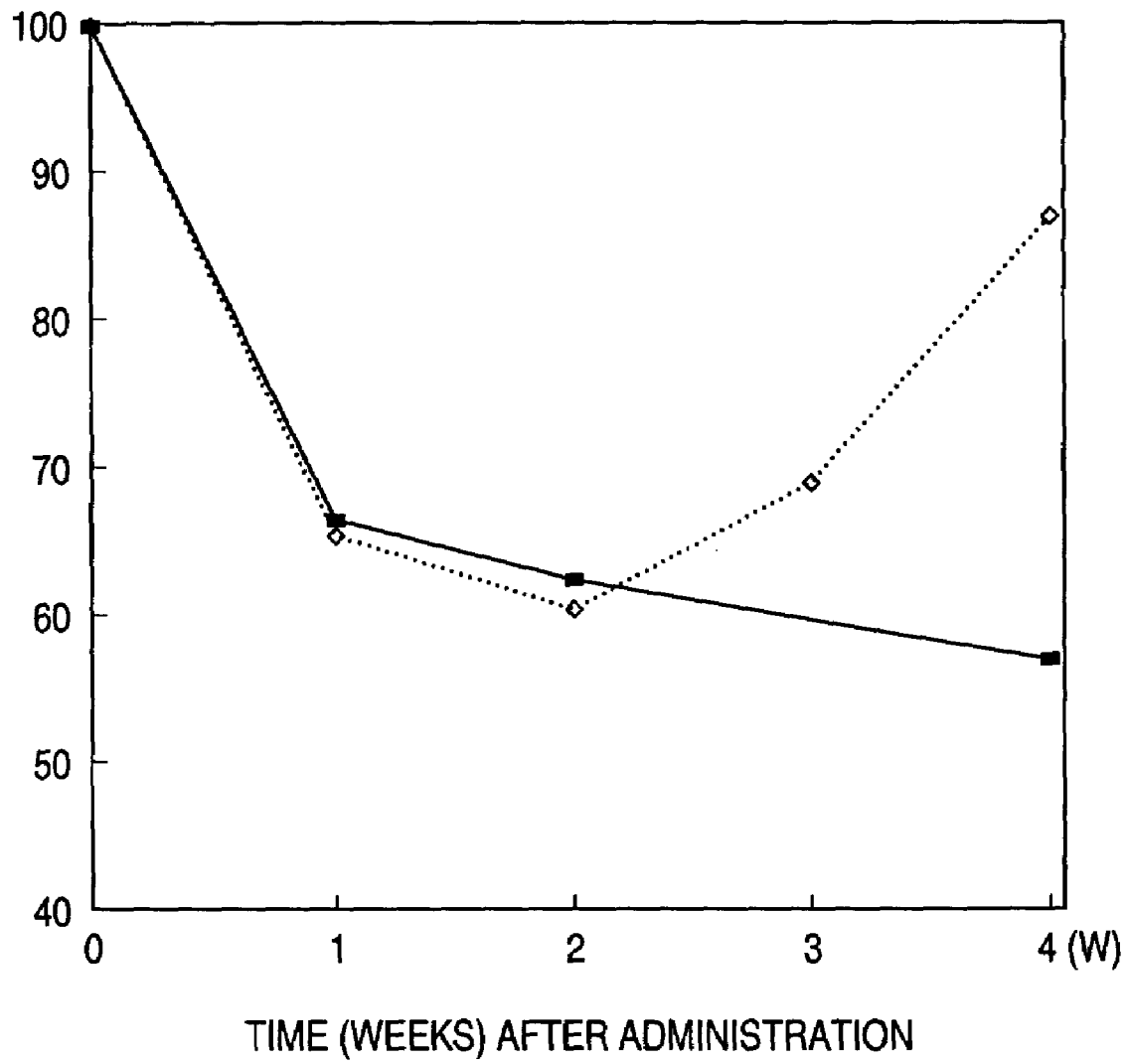
FIG. 3 shows changes in urinary Dpyr level (a bone resorption marker) in 4 weeks after the oral administration of the compound A (6 mg/day) in Example 5. In this figure, the abscissa indicates time (weeks) after the start of the administration, while the ordinate indicates the Dpyr level referring the Dpyr level before the administration as to 100%. The pamidronate data in this figure correspond to the clinical data of the intravenous injection of pamidronate (90 mg/4 weeks) (Lipton, A., Eur. J. Cancer, Vol. 34, 2021, 1998).

FIG. 3 shows changes in the Dpyr level serving as a bone resorption marker within 4 weeks after the administration. For comparison, clinical data of pamidronate intravenous injection marketed today (90 mg/4 weeks) are presented (Lipton, A., Eur. J. Cancer, Vo. 34, 2021, 1998). In the week 2, pamidronate showed a level corresponding to about 60% of the level before the administration. Subsequently, the bone resorption marker was increased and exceeded 80% after 4 weeks. On the other hand, the bone resorption marker was continuously regulated by the oral administration of the compound A and remained at 67 to 57% of the level before the administration after 1 to 4 weeks, thereby proving that the compound A has a stable and favorable effect of suppressing bone resorption.

Before the administration and after 12 and 24 weeks after the initiation of the administration, the systemic bone salt mass was measured. In 5 patients excluding one suffering from a failure in the measurement before the administration, the change ratio to the data before the administration attained 0.61% after 12 weeks and 1.18% after 24 weeks, showing an increase. Thus, it was confirmed that the bone mineral density was ameliorated. One of the patients showed an obvious amelioration in bone lesions in bone radiographs.

Narcotic scores ((a)×(b)), wherein (a) represents analgesic type (0: no, 1: nonsteroidal anti-inflammatory agent, 2: nonnarcotic analgesic, 3: narcotic, X: unknown); while (b) represents administration frequency (0: no, 1: less than once a day, 2: once a day, 3: twice or more a day, X: unknown), were calculated. As a result, a decrease in the narcotic score was observed (i.e., from 1.67±3.615 before the administration to 0.60±1.342 after 24 weeks), indicating that the bone pain was relieved and thus the amount of the analgesics employed was reduced.

A questionnaire on the QOL proposed by EORTC (European Organization for Research and Treatment of Cancer) was performed at the examination before the administration and after 24 weeks. As a result, improvement was observed in pain, fatigue, shortness of breath, inappetence, constipation, economic conditions, etc. No side effect the relation of which to the compound A was undeniable was observed in the 6 patients.

INDUSTRIAL APPLICABILITY

The "pharmaceutical compositions for treating bone lesions in multiple myeloma" according to the invention are superior to the existing BP compositions in the effect of treating bone lesions owing to both of the effect of suppressing bone resorption accompanying multiple myeloma and the effect of inhibiting myeloma of the compound according to the invention. Therefore, these compositions are useful in treating bone lesions in multiple myeloma (for example, bone pain, osteolysis, bone fracture, skeletal fracture, decrease in bone mineral density, etc.) and ameliorating accompanying bone-related symptoms (for example, frequency of radiotherapy, amount of analgesics used, performance of surgical operation, etc.).

The "pharmaceutical compositions for treating multiple myeloma" are useful as remedies for multiple myeloma having an additional effect of treating bone lesions in multiple myeloma.

It is expected that the above-described therapeutic effects of the pharmaceutical compositions according to the invention also contribute to the improvement in patients' QOL and affect the prognosis of patients such as the extension of the survival time. In fact, the results of the questionnaire on patients' QOL performed in the clinical test of Example 5 indicate that the patients' QOL had been improved.

Furthermore, the pharmaceutical compositions according to the invention exert favorable effects at a low dose and show little side effect. Accordingly, these compositions are highly useful in practice particularly as low-dose oral drugs with little side effect.

What claimed is:

1. A method for treating bone lesions in a patient suffering from multiple myeloma and bone lesions by both inhibiting proliferation of myeloma cells and suppressing bone resorption, comprising administering to said patient a pharmaceutically effective amount of 1-hydroxy-2-(imidazo[1,2-a]pyridin-3-yl)ethane-1,1-bisphosphonic acid or a salt thereof, and a pharmaceutically acceptable carrier or diluent.

2. The method of treating bone lesions according to claim 1, wherein 1-hydroxy-2-(imidazo[1,2-a]pyridin-3-yl)ethane-1,1-bisphosphonic acid or a salt thereof is administered orally in a dose of 1 to 20 mg per day.

3. The method of treating bone lesions according to claim 1, wherein 1-hydroxy-2-(imidazo[1,2-a]pyridin-3-yl)ethane-1,1-bisphosphonic acid or a salt thereof is administered orally in a dose of 3 to 10 mg per day.

4. A method of both inhibiting myeloma cell proliferation and suppressing bone resorption, comprising administering orally 1-hydroxy-2-(imidazo[1,2-a]pyridin-3-yl)ethane-1,1-bisphosphonic acid or a salt thereof in a dose of 1 to 20 mg per day to a patient suffering from multiple myeloma and bone lesions.

* * * * *